United States Patent [19]

McFarlane

[11] 4,365,630
[45] Dec. 28, 1982

[54] FLASHBACK CHAMBER FOR CATHETER
[76] Inventor: Richard H. McFarlane, 2571 Kaneville Rd., Geneva, Ill. 60134
[21] Appl. No.: 242,383
[22] Filed: Mar. 10, 1981
[51] Int. Cl.³ .............................................. A61M 5/00
[52] U.S. Cl. ................................ 128/214.4; 128/763; 128/771
[58] Field of Search .................... 128/349, 214, 214.4, 128/221, 760, 763–766, 771

[56] References Cited
U.S. PATENT DOCUMENTS

| 3,714,945 | 2/1973 | Stanley | 128/214.4 |
| 3,785,367 | 1/1974 | Fortin et al. | 128/763 |
| 4,187,860 | 2/1980 | Villari | 128/763 |
| 4,230,128 | 10/1980 | Aramayo | 128/763 |
| 4,292,970 | 10/1981 | Hession, Jr. | 128/214.4 X |

Primary Examiner—Stephen C. Pellegrino
Attorney, Agent, or Firm—John Cyril Malloy

[57] ABSTRACT

A plastic catheter is disclosed with an improved flashback chamber defining structure which structure includes (a) a main body portion providing a chamber maze for an interconnection between respective maze portions to insure a sequential filling of each portion with blood for visual observation of the flow of blood; (b) a top slidable transversely fluted cover is engaged in sealing relation of the main body portion by track defining structure defined by the main body portion for advancement of the plastic catheter in a patient's vein or artery, the cover being preferably of a transparent material to permit easy visual observation of the blood flow into the maze; and the catheter also includes a hollow needle secured to the leading end of the main body portion, the needly having flattened or oval portion captivatingly disposed in a cavity in the leading end; the cover having exterior flutes on the main body portion providing for non-slip advancement of the catheter relative to the needle, when the needle tip is in a proper location in a patient's vein or artery; and a positive stop is provided on the cover portion to prevent the exposure of any portion of the maze during the manipulation of the catheter; so that the overall disclosed structure results in coaxial alignment of the various parts while the catheter is being advanced.

17 Claims, 13 Drawing Figures

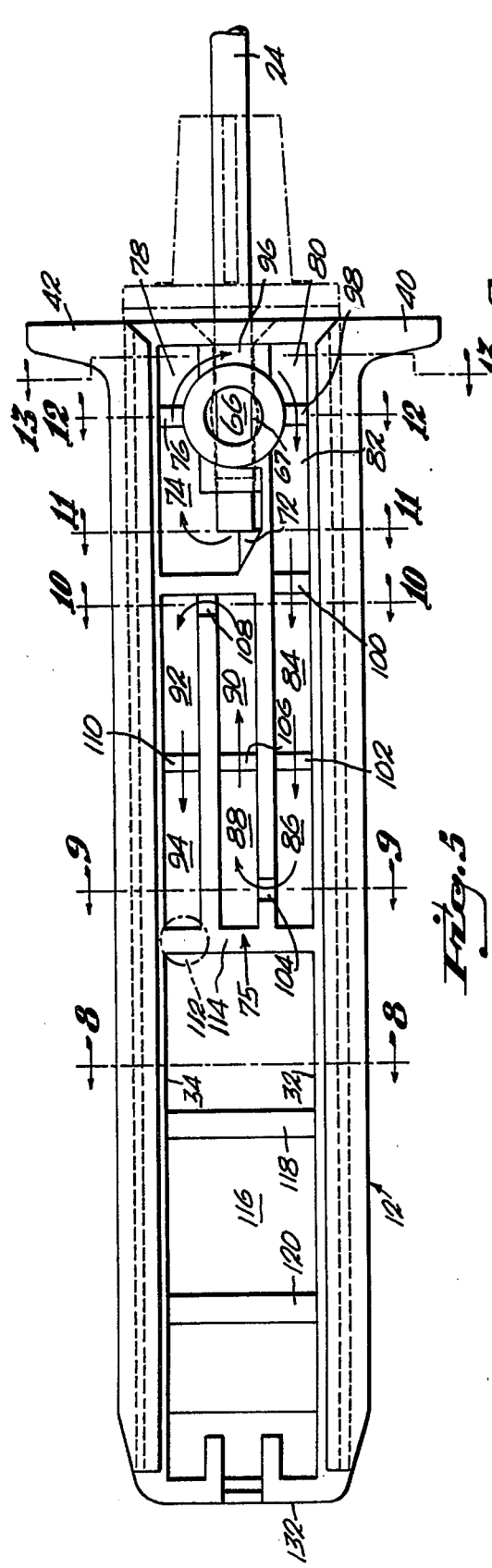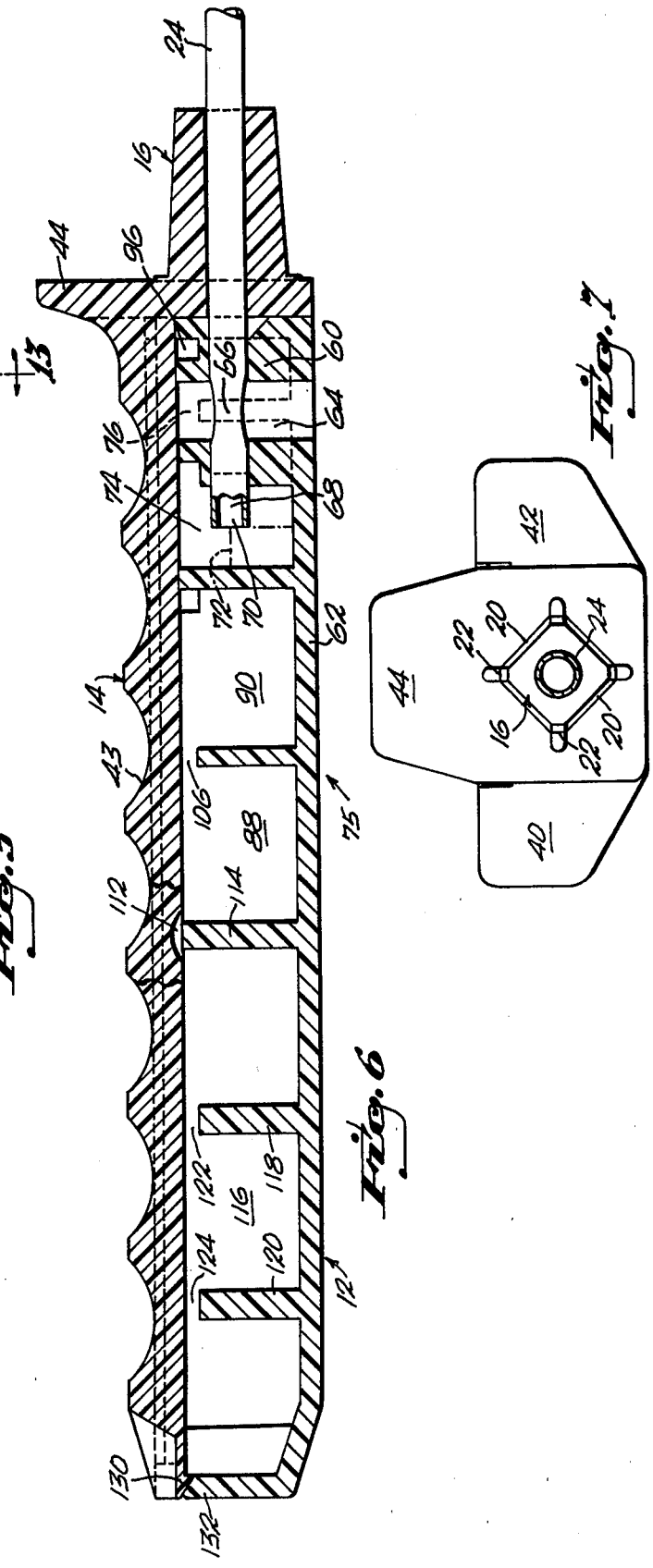

FLASHBACK CHAMBER FOR CATHETER

FIELD OF THE INVENTION

This invention relates, generally, to an improved flashback chamber for an associated catheter.

BACKGROUND OF THE INVENTION

The present invention relates to an improved flashback chamber structure for catheters. The flashback chamber of the present invention is constructed so as to permit the user to visually observe the relative rate of blood flow, to know if the flow is continuous, which in turn, indicates whether or not the needle tip is in a proper position in a vein or artery for subsequent advancement of the catheter coaxially with respect to a needle, which it slidably jackets, into the vein in which the needle tip has been properly positioned.

The flashback chamber structure, generally is composed of a main body portion which defines a blood receiving internal chamber subdivided into a maze or network or passageways of relatively small cross section. Preferably a slidable lid is in sealing engagement with the main body portion of the flashback chamber structure, in the preferred embodiment illustrated. To the lid or slide member, a hollow tube or plastic catheter is afixed so that it may be slidably advanced, or manipulated, relative to a needle, which it jackets by manipulating the slidable member.

More particularly a hollow needle is fixed relative to and extending outwardly of the forward end of the main body portion of the flashback chamber structure. The main body portion and slidable member are preferably provided with external gripping means which may be in the form of a pattern in relief, such as flutes. This accommodates coaxial movement of the lid or member relative to the main body portion as guided by guide means described hereinafter so that, after the needle point has been inserted correctly in a person's vein or artery, the catheter may be advanced without actually touching it during the advancement process and, hence, without the attendant danger of contaminating the same.

Within the main body portion, septums in a preferred embodiment are provided to define a relatively long blood path of relatively small cross sectional area, hereinafter referred to as chamber maze. In the preferred embodiment, an open mouth of the chamber structure is securely covered by a lid at all times during the needle and catheter insertion. The lid or slide member in a preferred embodiment is of suitable transparent plastic material to permit easy visual observation of the rate of blood flow into the passageways of the maze, that is, the blood path which is relatively long and of relatively small cross sectional area; thus, the visual progress of the blood flow ie, whether it is continuous or not, can be observed, which is an indication as to proper location of needle tip in a vein or artery prior to final advancement of the catheter.

OBJECTS OF THE INVENTION

It is an object of the present invention to provide an improved flashback chamber structure which structure included within the chamber means to define a relatively small cross sectional area and relatively long blood passageway, longer than the overall length of the flashback chamber structure, which may in one embodiment be composed of septums defining an interconnected maze, or passageways, so that the blood path is long and is progressively or sequentially filled with blood when the needle tip is inserted in a vein or artery.

Another object of the invention is to provide means to permit a visual observation of the blood flow as it sequentially fills the chamber portions of the maze.

A further object of the invention is to provide a secure gripping means on a main body portion of the catheter and the sliding lid to permit a convenient one hand operation of the catheter.

Yet another object of the invention is to provide a positive stop means to maintain the sliding lid in a covering and sealing relation to the maze during use.

There will be other objects of the present invention which will be apparent hereinafter, for example, most prior art flashback chambers define a relatively large chamber into which blood flows; however, one may not readily observe that the rate of flow of blood is continuous into the large chamber compared to one of a small cross sectional area where small changes in blood flow cause a linear movement of the leading edge of the blood. This avoids false flashbacks which have been a problem in the prior art for one attempting to properly position a needle in a vein or artery.

BRIEF DESCRIPTION OF THE DRAWINGS

FIG. 5 is a top plan view of the device of the present invention with the lid portion thereof removed;

FIG. 6 is a longitudinal vertical section view taken along line 6—6 of FIG. 2;

FIG. 7 is a front and elevational view of the device;

DESCRIPTION OF A PREFERRED EMBODIMENT

Figure 1:
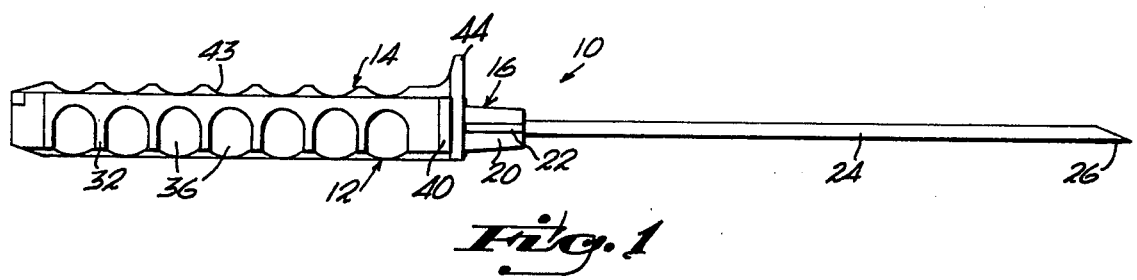
FIG. 1 is a side elevational view of the improved device embodying the present invention.
Figure 2:
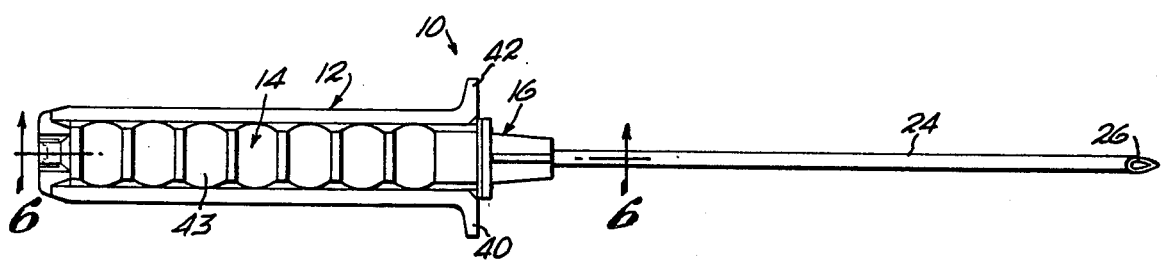
FIG. 2 is a top plan view of FIG. 1.

With reference to the drawings wherein a best mode is set forth, and particularly to FIGS. 1 and 2, the present invention, designated generally at 10. It includes a main body portion 12, and a sliding lid 14 provided with a forwardly extending tapered nose portion 16. The nose portion is adapted for slip-fitted engagement, companionately, within the open rear end of a conventional intravenous or IV catheter hub 18, see FIGS. 3 and 4. In a preferred embodiment, the nose portion 16 is defined by four equally sized and similarly configured flat faces 20, FIG. 7, with flattened connecting edges 22 therebetween.

An elongate hollow needle 24 is carried by the main body portion 12. It is slidably engaged through the nose portion 16 of the lid 14. The IV catheter hub 18 is conventionally, lengthwisely, sized to permit the forward pointed end 26 of the hollow needle 24 to normally project outwardly of the tapered front end 28 of the forward small diameter tubular portion 30 of the generally conventional IV connection catheter hub 18 and cannula, when said catheter hub is engaged on the nose portion 16, as in FIG. 3.

Figure 3:
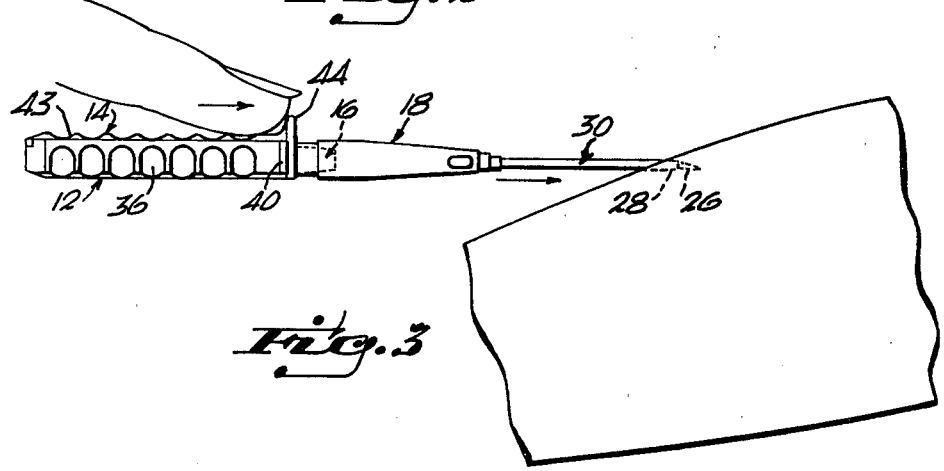
FIG. 3 is a view of the device as in FIG. 1 illustrating the insertion thereof into the arm of a patient with an intravenous catheter or cannula disposed on the hollow needle.
Figure 4:
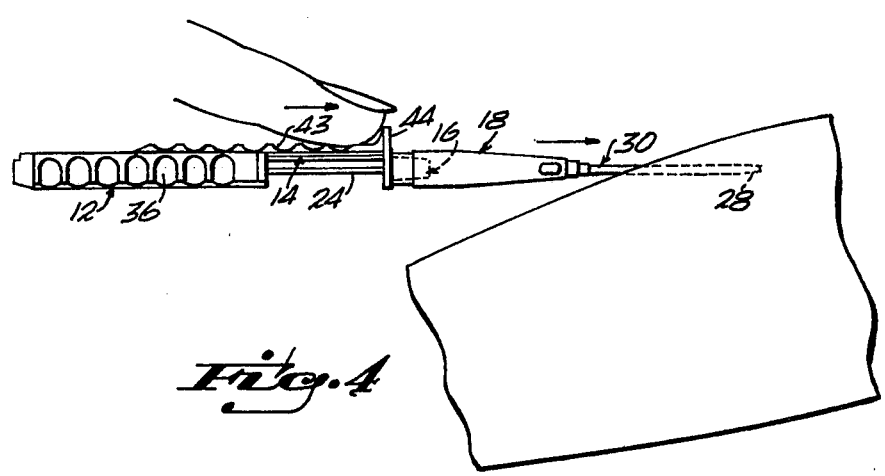
FIG. 4 is a view similar to FIG. 3 illustrating the fully inserted position.
Figure 8:
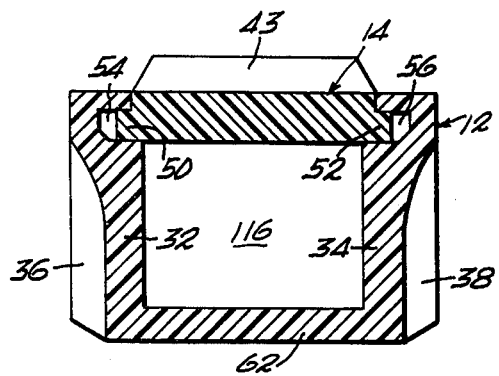
FIG. 8 is a cross sectional view taken along line 8—8 of FIG. 5.

It is this tip 26 of the needle which must be positioned correctly, prior to advancing the catheter by mainipulating the finger as indicated in FIG. 3 and FIG. 4 coaxially along the needle so that the flexible catheter catheter is what is actually inserted within the vein.

Figure 9:
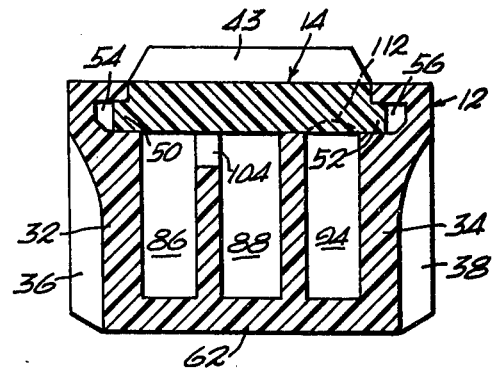
FIG. 9 is a cross sectional view taken along line 9—9 of FIG. 5.
Figure 10:
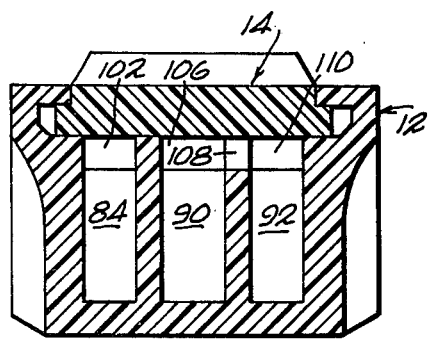
FIG. 10 is a cross sectional view taken along line 10—10 of FIG. 5.
Figure 11:
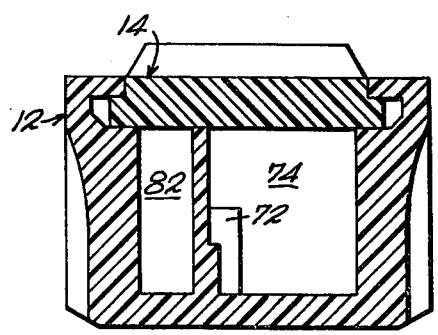
FIG. 11 is a cross sectional view taken along line 11—11 of FIG. 5.
Figure 12:
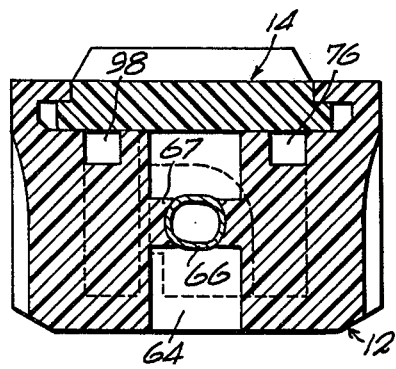
FIG. 12 is a cross sectional view taken along line 12—12 of FIG. 5.
Figure 13:
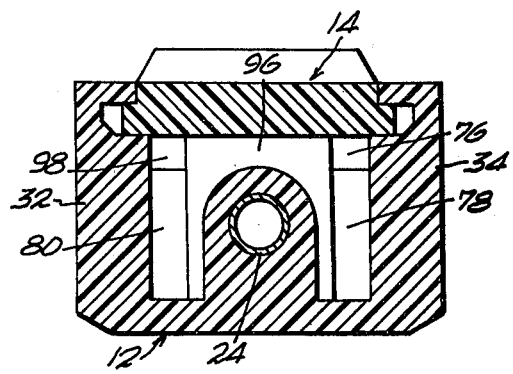
FIG. 13 is a cross sectional view taken along line 13—13 of FIG. 5.

The opposed side walls 32, 34, see FIG. 9, of the main body portion 12 include finger grip means such as the vertical flutes 36, 38, see FIG. 9, along their exterior lengths, terminating in a pair of oppositely outwardly extending forward end flanges 40, 42. The sliding lid 14 is transversely fluted along its length, as at 43, terminating in an upstanding forward end flange 44 or pusher means.

With particular reference to FIGS. 8 through 13, the lid 14 includes a pair of opposed side edge extensions 50, 52 for sliding but sealing engagement in mating longitudinally extending grooves 54, 56, defined in an opposed relation in the respective inner top edge portions of the side walls 32, 34 of the main body portion 12 and constituting track defining structure. By reason of this structure, the lid is urged into sealing sliding engagement with the main body during coaxial movement of the catheter, and needle by a user. It is thus seen that there has been provided mutually intercooperating guide track means which may take various forms, for example, instead of a continuous axially extending extension, 50 and 52, there may be provided tabs, in any event, providing for the guiding sliding coaxial movement of the lid relative to the main body portion.

In a preferred form, the hollow needle 24 extends slidably inwardly through the nose 16, and is securely anchored in front end upward web extension 60 from the bottom wall 62 of the main body portion 12. Extension 60 includes a vertical through hole 64 which is bisected by a flattened needle portion 66 between a pair of ears 67 to firmly secure the needle in place without the use of adhesive or the need for the needle to be insert molded into the structure described.

Flattened portion 66 defines the bulge as seen in FIG. 5, and does not interfere with the hollow passageway 68 therethrough, to an open inner end 70, which partially engages a limit abutment 72, formed within a first chamber 74 of a maze 75.

When blood from the open inner needle end 70 fills chamber 74, it flows through a top port 76 into a second maze chamber 78, and then sequentially into third, fourth, fifth, sixth, seventh, eighth, nineth, and tenth maze chambers 80, 82, 84, 86, 88, 90, 92 and 94 through respective top ports 96, 98, 100, 102, 104, 106, 108 and 110. The sliding lid 14 is formed of a suitable transparent plastic material to permit visual observation of the blood as it courses through the maze chambers and ports.

An air vent 112, see FIG. 6, in the underside of lid 14 spans a rear wall 114 of maze 75. This provides an opening between the last maze chamber 94 and a large rear end chamber 116 which includes a pair of transverse ribs 118, 120 which terminate short of the lid as at 122, 124. Thus when the needle is being inserted, and prior to the advancement of the catheter there is no air pressure which blocks blood flow into the passageways of the maze. However, once the lid is advanced, see FIG. 4, the bottom surface of the lid in abutting engagement with the rear wall 114 of the maze 75 will cause sealing to take place and avoid loss of blood.

Thus, this structure allows for escape of air from the maze when blood flows into it so as not to impede or block the blood flow. If the maze space is filled, then, blood may flow into the rear chamber 116.

Referring now to the left-hand side of FIG. 6, and to that portion designated by the numeral 130, it is seen that there is an angularly arranged stop projection 130, which extends downwardly from a rear edge of the lid 14 to a terminal edge close to but not actually at the rear wall 132 so as to provide for venting so that, when the lid is in a closed position, air within the cavity, i.e. the maze and chamber 116, as it is replaced by blood, may escape. It will also be seen that when the lid is advanced as shown in FIG. 4, this ame stop projection 130 will engage against the rear maze wall 114 when the catheter jacketing the needle is fully extended. Therefore, the entire maze 75, excluding of course, the rear chamber 116, is fully covered at all time when the catheter is in use.

When reference to FIG. 3, in use, the side walls 32, 34 of the main body portion 12 are grasped between the thumb and one finger. Next, the needle is inserted into the vein or artery of a patient. Proper positioning of the needle tip is determined by observing the blood flow into the maze. When the needle tip has been properly inserted, the flexible catheter jacketing the needle is moved forwardly, that is, advanced, by sliding the lid using the index finger, preferably, see FIG. 3, which advances the catheter into the patient's vein or artery. It is thus seen that the relatively slow sequential filling of the maze passageways, which are of relatively small cross sectional area, instead of a large cross sectional area, provides a clear visual observation of progress being made in the first initial step, represented by FIG. 3, of locating the needle tip in the vein or artery. The maze chamber portion may be colored or frosted to enhance the visual observation through the preferably transparent lid.

The air vent 112 provides an on-off valve means to control the flow of blood into the maze passageways 75. A very slight forward movement of the lid 14 closes the air vent 112 which communicates between the front maze and rear chamber portion 116 and, immediately, blood flow will stop.

The IV catheter normally remains in place in the vein for use as desired, after it has been inserted.

While a preferred form of the instant invention has been herein described, it will be obvious to those skilled in the art that various changes and modifications can be made therein without departing from the true spirit of the invention as defined in the appended claims. For example, various types structure may be utilized to provide the small cross sectional area network of passageways. The internal portion of the body portion may comprise members in threaded engagement wherein the threads do not completely fill the voids so that the blood is constrained to take a spiral path axially along the length of the device. Alternatively, the location of the vent hole, may be varied, or small passageway defining structure may be incorporated within the device within the spirit and scope of this invention.

What is claimed is:

1. An improved flashback structure for a catheter, said structure comprising; a main body portion including wall means defining a cavity; a member slidably engaged on said main body portion; means, within said cavity, defining a small cross sectional area blood path, said means defining said blood path comprising septum means defining a chamber maze within said body, an elongate hollow needle including a major forwardly extending length exteriorly of said main body portion; means securing said hollow needle to said main body portion, said needle terminating at a sharpened distal end, and including a minor rearwardly extending length secured within said main body portion; said hollow needle being in open communication with the interior of said flashback chamber structure cavity, whereby a fluid, such as blood, will flow through said hollow needle from said sharpened end, and into filling relation of said blood path, and said body portion including vent means to vent the blood path.

2. The improved device as defined in claim 1 wherein said device includes a catheter snugly and slidably jacketing said needle along the length thereof to the sharpened distal end and said catheter extending from said slidable member on said flashback structure and being connected thereto for advancing said catheter slidably and in coaxial relation with said needle.

3. The device as set forth in claim 1 outer surface of said main body portion and member include finger grip means.

4. The improved device as defined in claim 3 wherein said finger grip means comprises a plurality of transverse flutes.

5. The improved device as defined in claim 4 wherein said wall means terminate in oppositely outwardly extending flanges adjacent said means securing said hollow needle to said main body portion.

6. The improved device as defined in claim 4 wherein said member terminates at a front end in an upwardly extending flange adjacent said means securing said hollow needle to said main body portion.

7. The device as set forth in claim 1 wherein said main body portion includes a front, back, bottom, and opposed wall portions, and said member is slidably engaged on said opposed wall portions.

8. The improved device as defined in claim 1 wherein said means defining said blood path comprises a septum defining a first and second main chamber portion and said vent means comprises a port opening through said septum separating each pair of chamber portions of said maze.

9. The improved device as defined in claim 1 wherein said member includes means to limit sliding movement thereof between a first, fully closed position, relative to an open top side of a full length of said main body portion and a second, closed position relative to said maze.

10. The improved device as defined in claim 9 wherein said means to limit comprises, a downwardly angled projection from a rear edge of said member, said projection having a terminal end portion in close vented relation to said main body portion back wall in said first position.

11. The improved device as defined in claim 10 wherein said member includes a downwardly extending front wall including a forwardly projecting tapered nose portion provided with a through hole to permit free longitudinal coaxial movement of said member relative to said needle.

12. The improved device as defined in claim 11 wherein said nose portion is sized and configurated for a slip fit engagement within an open rear end of a conventional IV catheter hub.

13. The improved device as defined in claim 1 wherein said means to secure said needle minor length is within said main body portion.

14. The improved device as defined in claim 13 wherein said means to secure comprises the flattening of a portion of said needle, to a predetermined degree, between a pair of ears projecting oppositely outwardly from a wall of a vertical through hole in said main body front end portion.

15. The improved device as defined in claim 1 including stop means in said cavity to engage and position said needle inner end.

16. The improved device as defined in claim 1 wherein said vent means comprises an air vent defined in an underside of said slidable member.

17. An improved flashback structure for a catheter, said structure comprising; a main body portion including wall means defining a cavity; a member slidably engaged on said main body portion; means, within said cavity, defining a small cross sectional area blood path, said means defining said blood path comprising septum means defining a chamber maze within said body, an elongate hollow needle including a major forwardly extending length exteriorly of said main body portion; means securing said hollow needle to said main body portion, said needle terminating at a sharpened distal end, and including a minor rearwardly extending length secured within said main body portion; said hollow needle being in open communication with the interior of said flashback chamber structure cavity, whereby a fluid, such as blood, will flow through said hollow needle from said sharpened end, and into filling relation of said blood path, and said body portion including vent means to vent the blood path, said body portion and said member including a pair of opposed mating side edge portions for sliding and sealing engagement defining mating longitudinal guide means for said slidable member.

* * * * *